US012765771B2

(12) United States Patent
Cheng et al.

(10) Patent No.: US 12,765,771 B2
(45) Date of Patent: Oct. 20, 2026

(54) FUNDUS CAMERA

(71) Applicant: Medimaging Integrated Solution, Inc., Hsinchu (TW)

(72) Inventors: Chu-Ming Cheng, Hsinchu (TW); Wei-hsun Chang, Hsinchu (TW); Chun Yao Wang, Hsinchu (TW); Shao Hung Huang, Hsinchu (TW); Chien Kuan Chen, Hsinchu (TW)

(73) Assignee: Medimaging Integrated Solution, Inc., Hsinchu (TW)

( * ) Notice: Subject to any disclaimer, the term of this patent is extended or adjusted under 35 U.S.C. 154(b) by 750 days.

(21) Appl. No.: 17/854,819

(22) Filed: Jun. 30, 2022

(65) Prior Publication Data

US 2023/0000349 A1 Jan. 5, 2023

(30) Foreign Application Priority Data

Jun. 30, 2021 (TW) ................................ 110124055

(51) Int. Cl.
*A61B 3/12* (2006.01)
*A61B 3/00* (2006.01)
*A61B 3/14* (2006.01)

(52) U.S. Cl.
CPC .............. *A61B 3/12* (2013.01); *A61B 3/0008* (2013.01); *A61B 3/14* (2013.01)

(58) Field of Classification Search
CPC ................................ A61B 3/12; A61B 3/0008
USPC .................................................. 351/205, 206
See application file for complete search history.

(56) References Cited

U.S. PATENT DOCUMENTS

2010/0261966 A1* 10/2010 Reimer ................ G02B 26/023 362/277
2012/0050672 A1* 3/2012 Aikawa .................... A61B 3/14 351/206
2014/0063454 A1* 3/2014 Kamada .................. A61B 3/14 351/206
2014/0333896 A1* 11/2014 Ueno ....................... A61B 3/10 351/246
2016/0000324 A1* 1/2016 Rege ................... A61B 3/1208 600/479

(Continued)

*Primary Examiner* — Ricky L Mack
*Assistant Examiner* — Elizabeth M Hall
(74) *Attorney, Agent, or Firm* — MUNCY, GEISSLER, OLDS & LOWE, P.C.

(57) ABSTRACT

A fundus camera includes an objective lens, an illumination device, an imaging lens group and an image sensor. The illumination device has a light emitting position and includes a plurality of light emitting modules and a driving element. Each light emitting module generates a corresponding illumination light, and the optical characteristics of the illumination lights are different from each other. The driving element drives one of the light emitting modules to the light emitting position of the illumination device to output an illumination light with required optical characteristics and irradiate it to a fundus through the objective lens. The imaging light reflected by the fundus passes through the objective lens and the imaging lens group to form an image on the image sensor so as to generate a fundus image. The abovementioned fundus camera has a compact structure and can switch the illumination light sources in a short time to obtain fundus images with different optical characteristics.

13 Claims, 4 Drawing Sheets

(56) References Cited

U.S. PATENT DOCUMENTS

| | | | | |
|---|---|---|---|---|
| 2019/0269323 | A1* | 9/2019 | Cornsweet ........... | A61B 3/0091 |
| 2020/0345229 | A1* | 11/2020 | Huang ................. | A61B 3/0008 |

* cited by examiner

FUNDUS CAMERA

BACKGROUND OF THE INVENTION

1. Field of the Invention

The present invention relates to a fundus camera, particularly to fundus camera with several switchable illumination light sources.

2. Description of the Prior Art

The fundus camera has to introduce the illumination light source to pass through the pupil of the tested eyeball to the fundus for imaging. The light reflected from the fundus also passes through the pupil of the tested eyeball, imaged by an imaging system on the eye of the observer or an image sensor (or a film). The fundus camera may be used to observe whether the retina, the optical disc and the vasculature are abnormal.

The traditional fundus camera uses white light as the illumination light source. However, white light is a broadband light source. While the traditional fundus camera captures the image of a fundus, the fundus image is in fact a superimposition of fundus information generated by lights of a plurality of wavelengths. In such a case, some specified symptoms may be covered. In order to reveal a specified symptom, it is necessary to use an illumination light with a specified wavelength to illuminate the fundus. Nevertheless, a multi-light source illumination mechanism is bulky and makes the fundus camera hard to be miniaturized and inconvenient to be operated by hand.

Accordingly, many manufacturers are eager to develop a fundus camera with several switchable illumination light sources.

SUMMARY OF THE INVENTION

The present invention provides a fundus camera, which comprises a plurality of light emitting modules and uses a driving element to drive a specified light emitting module to a light emitting position to output an illumination light with required optical characteristics for capturing fundus images. The fundus camera of the present invention is compact in structure and able to quickly switch between different illumination light sources to acquire fundus images with different optical characteristics.

In one embodiment, the fundus camera of the present invention comprises an objective lens, an illumination device, an imaging lens group and an image sensor. The objective lens has a first side and a second side, and the first side faces the tested eyeball. The illumination device has a light emitting position and includes a plurality of light emitting modules and a driving element. Each light emitting module generates a corresponding illumination light. The optical characteristics of the lights generated by different light emitting modules are different. The driving element drives one of the light emitting modules to the light emitting position to output the illumination light with the required optical characteristics. The illumination light passes through the objective lens to illuminate the fundus of the tested eyeball, and the fundus reflects the illumination light to form an imaging light. The imaging lens group is coaxially disposed at the second side of the objective lens. The image sensor is disposed at a light output side of the imaging lens group. The imaging light passes through the objective lens and the imaging lens group in sequence and then focuses on the image sensor to form a fundus image.

The objective, technologies, features and advantages of the present invention will become apparent from the following description in conjunction with the accompanying drawings wherein certain embodiments of the present invention are set forth by way of illustration and example.

BRIEF DESCRIPTION OF THE DRAWINGS

The foregoing conceptions and their accompanying advantages of this invention will become more readily appreciated after being better understood by referring to the following detailed description, in conjunction with the accompanying drawings, wherein.

DESCRIPTION OF THE PREFERRED EMBODIMENTS

Various embodiments of the present invention will be described in detail below and illustrated in conjunction with the accompanying drawings. In addition to these detailed descriptions, the present invention can be widely implemented in other embodiments, and apparent alternations, modifications and equivalent changes of any mentioned embodiments are all included within the scope of the present invention and based on the scope of the Claims. In the descriptions of the specification, in order to make readers have a more complete understanding about the present invention, many specific details are provided; however, the present invention may be implemented without parts of or all the specific details. In addition, the well-known steps or elements are not described in detail, in order to avoid unnecessary limitations to the present invention. Same or similar elements in Figures will be indicated by same or similar reference numbers. It is noted that the Figures are schematic and may not represent the actual size or number of the elements. For clearness of the Figures, some details may not be fully depicted.

Figure 1:
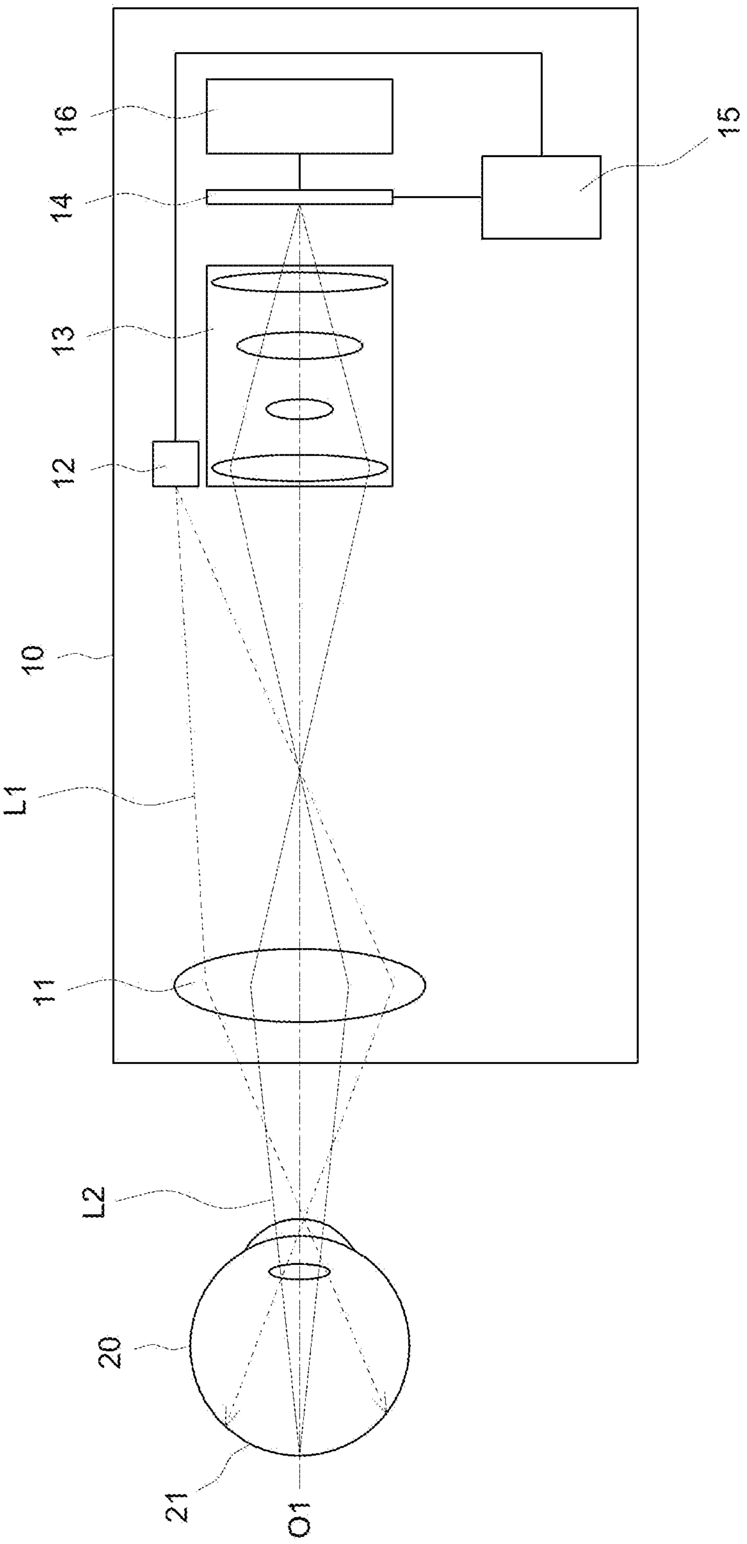
FIG. 1 is a diagram schematically showing a fundus camera according to a first embodiment of the present invention.

Refer to FIG. 1. In one embodiment, the fundus camera 10 of the present invention comprises an objective lens 11, an illumination device 12, an imaging lens group 13 and an image sensor 14. The objective lens 11 has a first side and a second side, and the first side faces a tested eyeball 20. The illumination device 12 generates an illumination light L1. The illumination light L1 passes through the objective lens 11 and projects onto a fundus 21 of the tested eyeball 20. In one embodiment, the illumination device 12 may be a coaxial illumination device. For example, the coaxial illumination device includes a hollow reflecting mirror or a ring-shape blocking plate, whereby while the illumination light passes through the pupil, it presents a ring-shape light spot coaxial with an optical axis O1; the imaging light, which is reflected by the fundus, penetrates from the central region of the ring-shape light spot. The coaxial illumination system also includes a relay lens. Thus, the total fundus camera is hard to be miniaturized. In one embodiment, as shown in FIG. 1, the illumination device 12 is an off-axis point-type illumination device. In other words, the illumination device 12 is deviated from the optical axis O1 of the objective lens 11. Besides, the illumination light L1 generated by the illumination device 12 is directly projected to the objective lens 11, whereby the relay lens, reflecting mirror, etc. are omitted. In one embodiment, the objective lens 11 may be a single biconvex lens, whereby to decrease the ghosting effect that is generated by the objective lens 11 reflecting the illumination light L1. The detailed structure of the illumination device 12 is to be described below.

The imaging lens group 13 is coaxially disposed at the second side of the objective lens 11. The image sensor 14 is disposed at a light output side of the imaging lens group 13. The fundus 21 reflects the illumination light L1 to form an imaging light L2. The imaging light L2 passes through the objective lens 11 and the imaging lens group 13 in sequence and then focuses on the image sensor 14 to form a fundus image. In one embodiment, the fundus camera 10 of the present invention further comprises a display device 16. The display device 16 is electrically connected with the image sensor 14 and able to present the fundus image output by the image sensor 14, whereby the operator can operate the fundus camera 10 or inspect the image quality of the fundus image.

Figure 2:
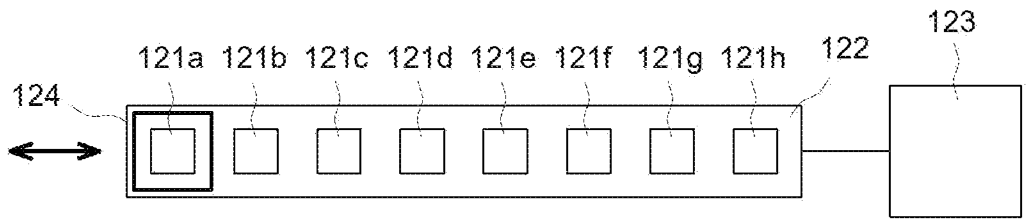
FIG. 2 is a diagram schematically showing an illumination device of a fundus camera according to the first embodiment of the present invention.

Refer to FIG. 2. In one embodiment, the illumination device includes a plurality of light emitting modules 121*a*, 121*b*, 121*c*, 121*d*, 121*e*, 121*f*, 121*g* and 121*h* and also includes a driving element 123. The light emitting modules 121*a*-121*h* may respectively generate illumination lights with different optical characteristics. For example, the light emitting modules 121*a*-121*h* may respectively generate illumination lights having different wavelength ranges, different polarization states, different light emitting angles, different light sources, or different combinations of the abovementioned optical characteristics. Bases on the fact that different tissues respectively absorb different spectra of lights, the signals respectively reflected by the tissues in different depths of the fundus are collected, and different signals may be combined to inspect abnormal symptoms. For example, green light may be used to detect fundus hemorrhage because blood vessels respond to green light more intensely; yellow-red lights are favorable to observe exudates of retinal pigment epithelium (RPE), such as drusen, or observe angiogenesis. A wider light emitting angle is favorable for operations, such as finding symptoms. A narrower light emitting angle can decrease the reflection from the interior of the system and focus on the area of interest. The light sources may be selected from light emitting diodes (LED), laser LED, superluminescent diodes (SLD), light bulbs, etc.

The driving element 123 drives at least one of the light emitting modules 121*a*-121*h* to a light emitting position 124, whereby to output an illumination light with the required optical characteristics. For example, the light emitting modules 121*a*-121*h* are disposed on a substrate 122; the driving element 123 drives the light emitting module 121*a* to the light emitting position 124 and makes the illumination device output an illumination light with the required optical characteristics. In the embodiment shown in FIG. 2, the driving element 123 moves the light emitting modules 121*a*-121*h* in a horizontal way, as indicated by the arrows.

Figure 3:
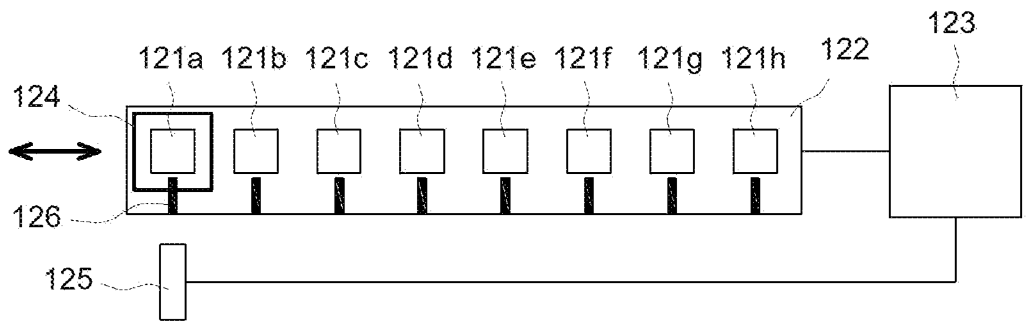
FIG. 3 is a diagram schematically showing an illumination device of a fundus camera according to a second embodiment of the present invention.

In one embodiment, the driving element 123 may be but is not limited to be a step motor or a motor with a position encoder, whereby the driving element 123 can accurately drive one of the light emitting modules 121*a*-121*h* to the light emitting position 124. Refer to FIG. 3. In one embodiment, the driving element 123 of the fundus camera of the present invention further includes a position detector 125. The position detector 125 can detect whether one of the light emitting modules 121*a*-121*h* is exactly corresponding to the light emitting position 124 and output a corresponding detection signal. According to the detection signal output by the position detector 125, the driving element 123 drives one of the light emitting modules 121*a*-121*h* to the light emitting position 124. In one embodiment, each of the light emitting modules 121*a*-121*h* has a positon label 126; the position detector 125 detects the position label 126 and outputs a corresponding detection signal. In one embodiment, the position label 126 may be a light-permeable hole, a light-reflecting surface, or a light-absorbing surface, which can generate an optical variation; the position detector 125 can detect the optical variation caused by the position label 126 and output a corresponding detection signal. In one embodiment, the position label 126 may be a spot or surface, which has relief structure or convex-concave structure to form spatial variation; the position detector 125 can detect the spatial variation and output a corresponding detection signal.

Figure 4:
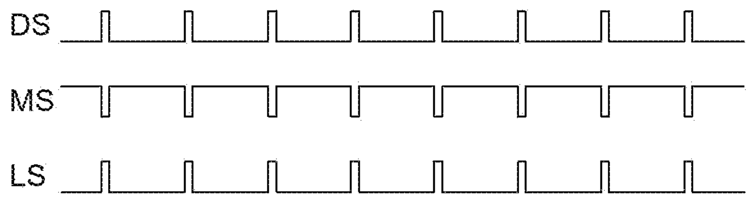
FIG. 4 is a diagram schematically showing control signals of an illumination device of a fundus camera according to the second embodiment of the present invention.

Refer to FIG. 4 for the control signals of the illumination device of the fundus camera of the present invention. In the embodiment shown in FIG. 3, the position detector 125 detects the position label 126 and outputs a corresponding detection signal DS. While the detection signal DS is at a high level, it indicates that the specified light emitting module 121*a* has moved to the light emitting position. Meanwhile, the driving element 123 may stop the rotation of the motor, i.e. the motor signal MS is at a low level, as shown in FIG. 4. While the required light emitting module 121*a* has been at the light emitting position 124, an illumination signal LS changes to be at a high level to control the light emitting module 121*a* to output the illumination light. Later, a next specified light emitting module is moved to the light emitting position to output an illumination light having required optical characteristics.

Figure 5:
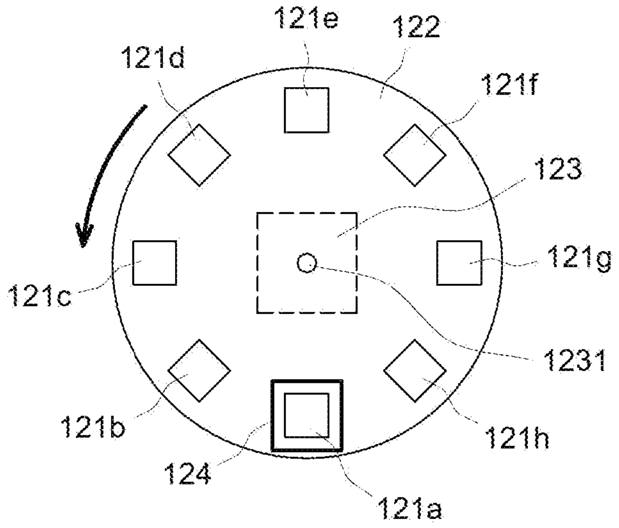
FIG. 5 is a diagram schematically showing an illumination device of a fundus camera according to a third embodiment of the present invention.
Figure 6:
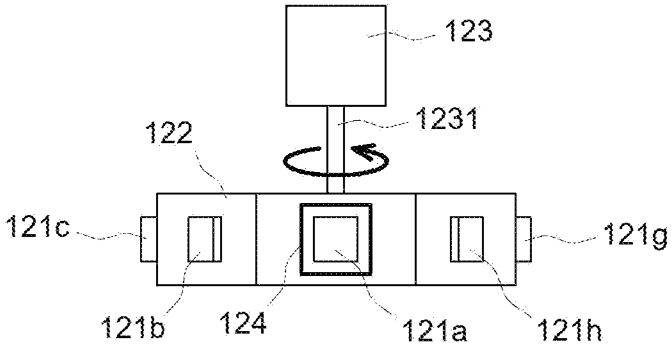
FIG. 6 is a diagram schematically showing an illumination device of a fundus camera according to a fourth embodiment of the present invention.

In the abovementioned embodiments, the driving element 123 moves the light emitting modules 121*a*-121*h* in a horizontal way. However, the present invention is not limited by these embodiments. Refer to FIG. 5 and FIG. 6. In one embodiment, the driving element 123 can drive the light emitting modules 121*a*-121*h* to the light emitting position 124 in a rotation way. For example, the driving element 123 may drive the light emitting modules 121*a*-121*h* to rotate with respect to a rotation axis 1231, as indicated by the arrow. In the embodiment shown in FIG. 5, the rotation axis 1231 is parallel to the optical axis O1 of the objective lens 11. In the embodiment shown in FIG. 6, the rotation axis 1231 is vertical to the optical axis O1 of the objective lens 11.

Figure 7:
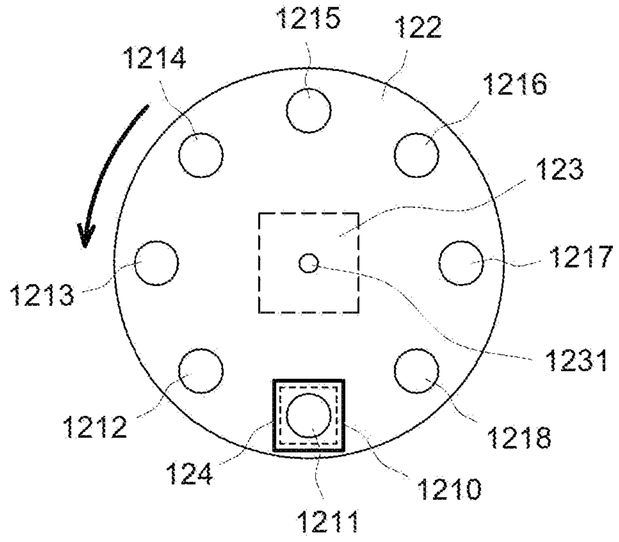
FIG. 7 is a diagram schematically showing an illumination device of a fundus camera according to a fifth embodiment of the present invention.

In one embodiment, the light emitting modules 121*a*-121*h* respectively include corresponding light emitting elements, which can separately generate illumination lights with different optical characteristics. For example, the light emitting elements may be respectively white light LED, red light LED, green light LED, etc. In one embodiment, the illumination lights having different optical characteristics may be generated by the cooperation of a light emitting element and a plurality of different optical elements. Refer to FIG. 7. In one embodiment, the illumination device includes a light emitting element 1210 and a plurality of optical elements 1211, 1212, 1213, 1214, 1215, 1216, 1217 and 1218; the light emitting element 1210 is disposed at a position corresponding to the light emitting position 124; the optical elements 1211-1218 may be filters or polarization plates. While the driving element 123 drives one of the optical elements 1211-1218 to a light output side of the light emitting element 1210, an illumination light with required optical characteristics can thus be output from the light emitting position 124. It is easily understood: the illumination device may include a plurality of light emitting elements and a plurality of optical elements. The driving element 123 may respectively drive a specified light emitting element and a specified optical element to the light emitting position, whereby the illumination device can output an illumination light with required optical characteristics.

Refer to FIG. 1 again. In one embodiment, the fundus camera of the present invention further comprises a processor 15. The processor 15 is electrically connected with the illumination device 12 and the image sensor 14. As shown in FIG. 4, the processor 15 can accurately control the motor signal MS to make a specified light emitting module move to the light emitting position according to the detection signal DS; then the illumination signal LS enables the image sensor 14 to capture the fundus image having required optical characteristics. Therefore, the processor 15 can control the illumination device to generate illumination lights with different optical characteristics in a programmable way during an image-capturing interval, whereby the fundus camera can capture fundus images of different optical characteristics. In one embodiment, the image-capturing interval is shorter than or equal to one second. Based on the abovementioned structure, the fundus camera of the present invention can thus capture a plurality of fundus images of different optical characteristics in a short time. Therefore, the present invention not only can shorten the time of inspection but also can prevent the image quality from being affected by the swing generated by changing the light sources. Thus, the fundus camera of the present invention can be held by hand for operation.

In conclusion, the fundus camera of the present invention comprises a plurality of light emitting modules, and a driving element drives a specified light emitting module to a light emitting position to output an illumination light with required optical characteristics for capturing fundus images. The appropriate design of the illumination device and the programmable operation makes the fundus camera of the present invention is compact in structure and able to switch the illumination light sources in a short time for acquiring fundus images of different optical characteristics.

While the invention is susceptible to various modifications and alternative forms, a specific example thereof has been shown in the drawings and is herein described in detail. It should be understood, however, that the invention is not to be limited to the particular form disclosed, but to the contrary, the invention is to cover all modifications, equivalents, and alternatives falling within the appended claims.

What is claimed is:

1. A fundus camera, comprising
- an objective lens, having a first side and a second side, wherein the first side faces a tested eyeball;
- an illumination device, having a light emitting position and including
  - a plurality of light emitting modules, respectively generating corresponding illumination lights separately having different optical characteristics, wherein the light emitting modules are provided in a linear form and arranged in a direction which is vertical to an optical axis of the objective lens; and
  - a driving element, driving one of the plurality of light emitting modules to the light emitting position to generate the illumination light with required optical characteristics, wherein the illumination light passes through objective lens to project onto a fundus of the tested eyeball and is reflected by the fundus to form an imaging light;
- an imaging lens group, coaxially disposed at the second side of the objective lens; and
- an image sensor, disposed at a light output side of the imaging lens group, wherein the imaging light passes through the objective lens and the imaging lens group and then focuses on the image sensor to form a fundus image;
- a processor, electrically connected with the illumination device and the image sensor, wherein the processor controls the illumination device to generate the illumination lights of different optical characteristics to capture fundus images of different optical characteristics;
- wherein, the driving element further includes a position detector, and wherein the position detector detects whether one of the plurality of light emitting modules is corresponding to the light emitting position and outputs a corresponding detection signal, and wherein the driving element drives one of the plurality of light emitting modules to the light emitting position according to the detection signal.

2. The fundus camera according to claim 1, wherein the driving element drives the plurality of light emitting modules in a horizontal way.

3. The fundus camera according to claim 1, wherein the driving element includes a step motor or a motor with a position encoder.

4. The fundus camera according to claim 1, wherein each of the plurality of light emitting modules includes a position label, and the position detector detects the position label to output the corresponding detection signal.

5. The fundus camera according to claim 4, wherein the position label generates an optical variation or a spatial variation, which is to be detected by the position detector.

6. The fundus camera according to claim 1, wherein the illumination device includes a plurality of light emitting elements functioning as the plurality of light emitting modules; the plurality of light emitting elements respectively generates the illumination lights separately having different optical characteristics.

7. The fundus camera according to claim 1, wherein the illumination device includes
- a light emitting element, disposed at the light emitting position; and
- a plurality of optical elements, each cooperating with the light emitting element to form a corresponding one of the plurality of light emitting modules, wherein the driving element drives one of the plurality of optical elements to a light output side of the light emitting element for outputting an illumination light with required optical characteristics.

8. The fundus camera according to claim 1, wherein the illumination device includes a plurality of light emitting elements; and a plurality of optical elements, respectively cooperating with the plurality of light emitting elements to form the plurality of light emitting modules correspondingly, wherein the driving element drives at least one of the plurality of light emitting elements and the plurality of optical elements to the light emitting position for outputting an illumination light with required optical characteristics.

9. The fundus camera according to claim 1, wherein the optical characteristics of the illumination light include wavelength ranges, polarization states, light emitting angles, light sources, or combinations thereof.

10. The fundus camera according to claim 1, wherein the light emitting position is deviated from the optical axis of the objective lens for outputting an off-axis direct illumination light.

11. The fundus camera according to claim 1, wherein the light emitting modules include light emitting diodes (LED), laser LED, superluminescent diodes (SLD), or light bulbs.

12. The fundus camera according to claim 1, wherein the objective lens is a single biconvex lens.

13. The fundus camera according to claim 1, further comprising a display device, electrically connected with the image sensor to present the fundus image formed by the image sensor.

* * * * *